(12) United States Patent
Bowman et al.

(10) Patent No.: US 7,681,467 B2
(45) Date of Patent: Mar. 23, 2010

(54) DENSE PACKED SAMPLING TOOL

(75) Inventors: David J. Bowman, Charlotte, NC (US); Benjamin D. Underwood, Albermarle, NC (US); Bohdan Boyko, Williamsburg, VA (US)

(73) Assignee: US GreenFiber, LLC, Charlotte, NC (US)

( * ) Notice: Subject to any disclaimer, the term of this patent is extended or adjusted under 35 U.S.C. 154(b) by 229 days.

(21) Appl. No.: 11/319,041

(22) Filed: Dec. 27, 2005

(65) Prior Publication Data

US 2007/0144275 A1    Jun. 28, 2007

(51) Int. Cl.
*G01N 1/04* (2006.01)
(52) U.S. Cl. .................................... 73/864.44
(58) Field of Classification Search .............. 73/864.44, 73/864.45
See application file for complete search history.

(56) References Cited

U.S. PATENT DOCUMENTS

| | | | | | |
|---|---|---|---|---|---|
| 2,346,220 | A | * | 4/1944 | Kienzle et al. | 73/864.44 |
| 3,291,231 | A | * | 12/1966 | Kammer | 175/170 |
| 3,444,938 | A | * | 5/1969 | Ballmann | 111/101 |
| 3,515,230 | A | * | 6/1970 | Tomaine | 175/242 |
| 4,516,438 | A | * | 5/1985 | Hodge | 73/864.44 |
| 4,549,612 | A | * | 10/1985 | Cushing | 175/20 |
| 4,779,689 | A | * | 10/1988 | Paxton, III | 175/403 |
| 4,884,638 | A | * | 12/1989 | Hoffman | 172/22 |
| 4,887,413 | A | * | 12/1989 | Tuckey, Jr. | 53/520 |
| 5,005,433 | A | * | 4/1991 | Patton | 73/864.44 |
| 6,102,135 | A | * | 8/2000 | Shaw | 175/20 |
| 6,449,825 | B1 | * | 9/2002 | Dodge, Sr. | 29/402.01 |
| 6,659,195 | B2 | * | 12/2003 | Schmon | 175/20 |

OTHER PUBLICATIONS

Owens Corning Innovations For Living; information from the internet, copyright 1996-2004.
ebuild The Professional's Guide to Building Products; information from the internet; published Jul. 1, 2004.

* cited by examiner

*Primary Examiner*—Robert R Raevis
(74) *Attorney, Agent, or Firm*—MacCord Mason PLLC

(57) ABSTRACT

A sampling apparatus for taking a core sample of dense packed fibrous material including: (a) a generally cylindrical sampling tube open on its distal end, wherein the length of the sampling tube is greater than the sample length; (b) at least one exhaust port outside the sampling length adjacent to its proximate end; (c) a ram rod movable from the proximate end to the distal end of the sampling tube for discharging a sample from the sampling tube; and (d) a drive attached to the proximate end of the sampling tube for aiding in sampling.

26 Claims, 2 Drawing Sheets

DENSE PACKED SAMPLING TOOL

BACKGROUND OF THE INVENTION (1) Field of the Invention

The present invention relates generally to sampling tools and more particularly to a sampling tool for taking a core sample of dense packed fibrous material.

(2) Description of the Prior Art

Traditionally sprinkler systems and smoke detectors may be installed in both residential and commercial buildings to detect and stop fires. However, other fire retardant products are commercially available for use in buildings. For instance, cellulose material may be used around openings and other non-combustion venting areas to help prevent fire. To do so, the cellulose must be densely packed to a density specified by local and national fire codes. In order to pass inspection by the building inspector, builders must be able to withdraw samples of the installed cellulose in order to determine whether the density is up to code.

Thus, there remains a need for a new and improved dense packed sampling tool, which is easy to operate and use.

SUMMARY OF THE INVENTION

The present invention is directed to a sampling apparatus for taking a core sample of dense packed fibrous material. The apparatus may include: (a) a generally cylindrical sampling tube open on its distal end, wherein the length of the sampling tube is greater than the sample length; (b) at least one exhaust port outside the sampling length adjacent to its proximate end; (c) a ram rod movable from the proximate end to the distal end of the sampling tube for discharging a sample from the sampling tube; and (d) a drive attached to the proximate end of the sampling tube for aiding in sampling.

In the preferred embodiment, the leading edge of the distal end of the sampling tube may form a kerf in the material being sampled. The kerf aids the penetration of the sampling tube into the material being sampled. Preferably, the leading edge of the sampling tube may be serrated. The depths of the serrations are preferably sufficient to permit material removal during sampling.

Preferably, the exhaust port may be located on the end wall of the proximate end of the sampling tube to permit limited access.

Also in the preferred embodiment, the ramrod may extend the entire length of the sample tube. Preferably, the cross-sectional area of the ramrod may be between 5 and 95% of the cross-sectional area of the inside diameter of the sampling tube. Also preferably, the outside diameter of the ramrod may be sized to the inside diameter of the sampling tube. In the preferred embodiment, the distal end of the ramrod may be substantially flat. The ramrod may also further include a handle attached to its proximate end.

In the preferred embodiment, the drive may be a rotary drive. The rotary drive may include a motor. The motor may be electrically powered. Preferably, the rotary drive may further include an arbor. Also preferably, the drive may include a quick disconnect between the drive and the sampling tube.

Accordingly, one aspect of the present invention is to provide a sampling apparatus. The apparatus may include: (a) a generally cylindrical sampling tube open on its distal end, wherein the length of the sampling tube is greater than the sample length; and (b) at least one exhaust port outside the sampling length adjacent to its proximate end.

Another aspect of the present invention is to provide a sampling apparatus for taking a core sample of dense packed fibrous material. The apparatus may include:
(a) a generally cylindrical sampling tube open on its distal end wherein the length of the sampling tube may be greater than the sample length; (b) at least one exhaust port outside the sampling length adjacent to its proximate end; and a ramrod movable from the proximate end to the distal end of the sampling tube for discharging a sample from the sampling tube.

Still another aspect of the present invention is to provide a sampling apparatus for taking a core sample of dense packed fibrous material. The apparatus may include: (a) a generally cylindrical sampling tube open on its distal end, wherein the length of the sampling tube is greater than the sample length; (b) at least one exhaust port outside the sampling length adjacent to its proximate end; (c) a ram rod movable from the proximate end to the distal end of the sampling tube for discharging a sample from the sampling tube; and (d) a drive attached to the proximate end of the sampling tube for aiding in sampling.

These and other aspects of the present invention will become apparent to those skilled in the art after a reading of the following description of the preferred embodiment when considered with the drawings.

DESCRIPTION OF THE PREFERRED EMBODIMENTS

Figure 1:
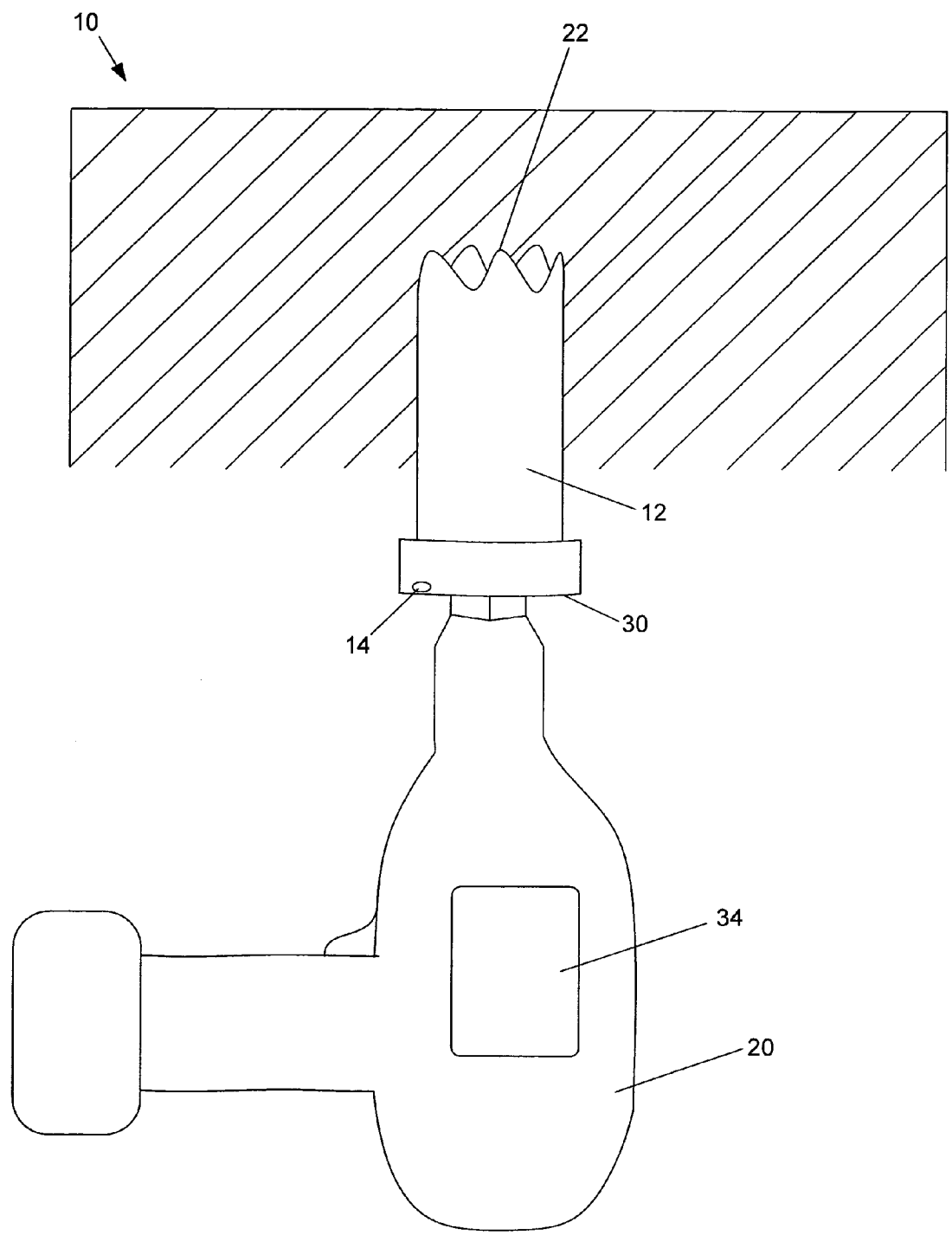
FIG. 1 is a drawing illustrating a dense packed sampling tool inserted into densely packed installed material.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto.

As best seen in FIG. 1, the sampling apparatus 10 is seen cutting into a cross-sectional view of the installed material. The sampling apparatus 10 includes a sample tube 12, an exhaust port 14, a ramrod 16 (best seen in FIG. 3), and a drive 20. The sample tube 12 has a leading edge on the distal end 22 that may form a kerf as the tube moves through the material. In the preferred embodiment, the sampling tube 12 has a serrated leading edge on the distal end 22. The serrations may help form the kerf. A kerf can help the sample tube 12 to be fully inserted into the material. Without a kerf, it may take excessive force to fully insert the sample tube 12. Further, the material may smolder if a kerf is not formed.

The installed material may have discrete elements, and may be selected from the group consisting of fibrous material, granular material, pellet material and agglomerated material. The material may be inorganic. For example, the inorganic material may be selected from the group consisting of fiberglass, rock wool, pearlite, mineral wool, and asbestos. The material may include organic materials such as cellulose, polystyrene, and polyurethane. The material also may be an organic material such as a natural cellulosic material.

In an embodiment, the material may be a non-conductive insulation material. The non-conductive material may be one or more of thermally non-conductive materials, acoustically non-conductive materials and electrically non-conductive materials.

Also in the preferred embodiment, the exhaust port 14 is located on the end wall 30 to permit limited access.

Figure 2:
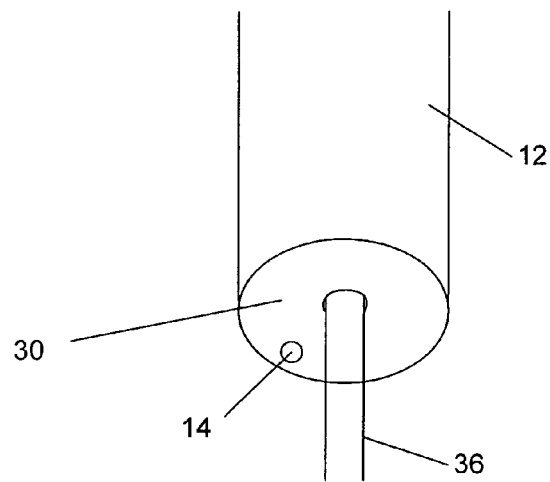
FIG. 2 is a perspective view of the arbor as attached to the sampling tube.

In the preferred embodiment, the drive 20 is a rotary drive. The drive 20 includes a motor 34, and is electrically powered. Preferably, the drive also includes an arbor 36 as best seen in FIG. 2. The drive 20 includes a quick disconnect between the drive 20 and the sample tube 12.

Figure 3:
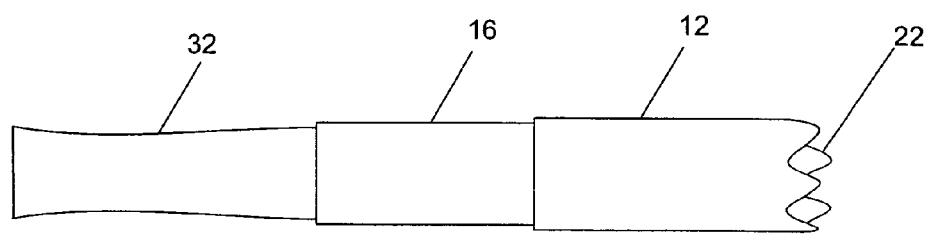
FIG. 3 is a side view of the ramrod being inserted into the sampling tube.

As best seen in FIG. 3, the ramrod 16 includes a handle attached to the end 32. Preferably, the ramrod 16 extends the entire length of the sample tube 12. The cross-sectional area of the ramrod 16 is between 5 and 95% of the cross-sectional area of the inside diameter of the sampling tube 12. The outside diameter of the ramrod is sized to the inside diameter of the sampling tube 12. The distal end of the ramrod 16 is substantially flat. The ramrod 16 is used for reinserting the material after the density of the sample has been determined. The ramrod 16 provides enough force to ensure the material is inserted at a proper density.

Figure 4:
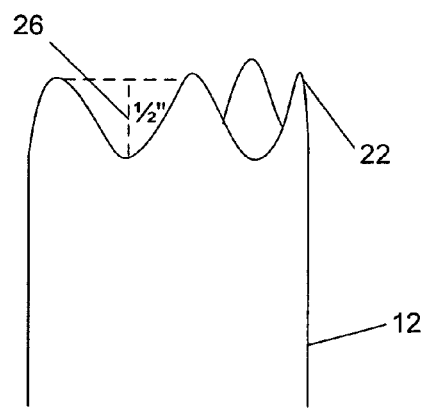
FIG. 4 is an enlarged view of the serrated edge of the sampling tube.

Turning now to FIG. 4, the serrated leading edge of the sampling tube 12 is shown. The depth 26 must be sufficient to permit material removal. Preferably, the serrations are formed with eight periodicities of one half-inch depth. Other periodicities may be used, but will not work as effectively. The following table shows the level of perceived efficiency of three different embodiments of the serrations on the sampling tube. The depth must be sufficient to permit removal of the material. However, the serrations are preferably not sharpened to prevent breaching the structure behind the material being sampled.

TABLE 1

| No sharpening, No depth, No spacing of serrations | Serrations with 2-3 periodicities of $3/16$ inch depth. | Serrations with 8 periodicities of $1/2$ inch depth. |
|---|---|---|
| Inefficient | Moderately efficient | Most efficient |

Certain modifications and improvements will occur to those skilled in the art upon a reading of the foregoing description. By way of example, to sample fiberglass it would be necessary to sharpen the leading edge of the sample tube into a cutting edge.

It should be understood that all such modifications and improvements have been deleted herein for the sake of conciseness and readability but are properly within the scope of the following claims.

We claim:

1. A rotary sampling apparatus for sampling the installed density of an insulative material installed adjacent to a building structure by obtaining a sample length, said apparatus comprising:
    (a) a generally cylindrical sampling tube open on its distal end, wherein the length of the sampling tube is greater than the sample length;
    (b) an end wall that has a surface approximately perpendicular to the longitudinal axis of the tube, the surface including at least one exhaust port outside the sampling length, said exhaust port adapted to both permit the unobstructed egress of air therethrough, and to exhaust air directly from the port into the ambient;
    (c) at least one serration on the distal end of the sampling tube, wherein the at least one serration is configured to cut into the installed insulative material and to prevent breaching the adjacent building structure; and
    (d) a drive attached to the proximate end of the sampling tube for aiding in sampling, wherein the drive includes a quick disconnect between the drive and the sampling tube.

2. The apparatus according to claim 1, wherein the drive is a rotary drive.

3. The apparatus according to claim 2, wherein the rotary drive includes a motor.

4. The apparatus according to claim 3, wherein the motor is electrically powered.

5. The apparatus according to claim 2, wherein the rotary drive further includes an arbor.

6. The apparatus according to claim 1, wherein the at least one serration has depth of about $3/16$" to about $1/2$", and defines a substantially rounded point being sharp enough to cut through the installed insulative material yet dull enough to minimize cutting the adjacent building structure.

7. The apparatus according to claim 6, wherein the at least one serration includes about 2 to about 8 serrations.

8. The apparatus according to claim 1, wherein the exhaust port is located on the end wall of the proximate end of the sampling tube to permit limited access to a sample contained within the sampling tube.

9. A rotary sampling system for taking a sample length of dense packed fibrous material installed adjacent to a building structure, said system comprising:
    (a) a generally cylindrical sampling tube open on its distal end wherein the length of the sampling tube is greater than the sample length;
    (b) an end wall that has a surface approximately perpendicular to the longitudinal axis of the tube, the surface including at least one exhaust port outside the sampling length, said exhaust port adapted to both permit the unobstructed egress of air therethrough, and to exhaust air directly from the port into the ambient;
    (c) a ramrod movable from the proximate end to the distal end of the sampling tube for discharging a sample from the sampling tube;
    (d) at least one serration on the distal end of the sampling tube, wherein the at least one serration is configured to cut into the installed insulative material and to prevent breaching the adjacent building structure; and
    (e) a rotary drive attached to the proximate end of the sampling tube for aiding in sampling, the rotary drive including a motor.

10. The system according to claim 9, wherein the ramrod extends the entire length of the sample tube.

11. The system according to claim 9, wherein the cross-sectional area of the ramrod is between 5 and 95% of the cross-sectional area of the inside diameter of the sampling tube.

12. The system according to claim 9, wherein the outside diameter of the ramrod is sized to fit within the inside diameter of the sampling tube.

13. The system according to claim 12, wherein the distal end of the ramrod is substantially flat.

14. The system according to claim 9, wherein the ramrod further includes a handle attached to its proximate end.

15. A rotary sampling system for taking a sample length of dense packed fibrous material installed adjacent to a building structure, said system comprising:
   (a) a generally cylindrical sampling tube open on its distal end, wherein the length of the sampling tube is greater than the sample length;
   (b) an end wall that has a surface approximately perpendicular to the longitudinal axis of the tube, the surface including at least one exhaust port outside the sampling length, said exhaust port adapted to both permit the unobstructed egress of air therethrough, and to exhaust air directly from the port into the ambient;
   (c) a ram rod attachable to the sampling tube and movable from the proximate end to the distal end of the sampling tube for discharging a sample from the sampling tube;
   (d) a rotary drive attachable to the proximate end of the sampling tube for aiding in sampling, the rotary drive including a motor, and
   (e) at least one serration on the distal end of the sampling tube, wherein the at least one serration is configured to cut into the installed insulative material and to prevent breaching the adjacent building structure.

16. The system according to claim 15, wherein the motor is electrically powered.

17. The system according to claim 15, wherein the rotary drive further includes an arbor.

18. The system according to claim 15, wherein the drive includes a quick disconnect between the drive and the sampling tube.

19. The system according to claim 15, wherein the leading edge of the sampling tube is serrated.

20. The system according to claim 19, wherein the depth of the serrations are sufficient to permit material removal during sampling.

21. The system according to claim 15, wherein the exhaust port is located on the end wall of the proximate end of the sampling tube to permit limited access to a sample contained within the sampling tube.

22. The system according to claim 21, wherein the ramrod extends the entire length of the sample tube.

23. The system according to claim 21, wherein the cross-sectional area of the ramrod is between 5 and 95% of the cross-sectional area of the inside diameter of the sampling tube.

24. The system according to claim 21, wherein the outside diameter of the ramrod is sized to fit within the inside diameter of the sampling tube.

25. The system according to claim 24, wherein the distal end of the ramrod is substantially flat.

26. The system according to claim 15, wherein the ramrod further includes a handle attached to its proximate end.

* * * * *